United States Patent [19]

Ebetino et al.

[11] Patent Number: 5,071,840

[45] Date of Patent: Dec. 10, 1991

[54] CERTAIN HETEROCYCLIC SUBSTITUTED DIPHOSPHONATE COMPOUNDS PHARMACEUTICAL COMPOSITIONS, AND METHODS OF TREATING ABNORMAL CALCIUM AND PHOSPHATE METABOLISM

[75] Inventors: Frank H. Ebetino, Norwich, N.Y.; James J. Benedict, Golden, Colo.

[73] Assignee: Norwich Eaton Pharmaceuticals, Inc., Norwich, N.Y.

[21] Appl. No.: 378,530

[22] Filed: Jul. 11, 1989

Related U.S. Application Data

[63] Continuation-in-part of Ser. No. 945,068, Dec. 19, 1986, abandoned.

[51] Int. Cl.$^5$ .................. C07F 9/38; A61K 31/675
[52] U.S. Cl. .......................... 514/89; 546/22; 544/214; 544/243; 544/337
[58] Field of Search ............................. 546/22; 514/89

[56] References Cited

U.S. PATENT DOCUMENTS

| | | | |
|---|---|---|---|
| 3,957,160 | 5/1976 | Ploger et al. .................. | 210/58 |
| 3,960,888 | 6/1976 | Ploger et al. .................. | 548/412 |
| 4,034,086 | 7/1977 | Ploger et al. .................. | 514/91 |
| 4,687,767 | 8/1987 | Bosies et al. .................. | 514/89 |
| 4,696,920 | 9/1987 | Bentzen et al. ................ | 514/89 |
| 4,719,203 | 1/1988 | Bosies et al. .................. | 514/108 |
| 4,857,513 | 8/1989 | Oku et al. ..................... | 514/76 |

FOREIGN PATENT DOCUMENTS

| | | | |
|---|---|---|---|
| 8781451 | 5/1988 | Australia .................. | 546/23 |
| 8781453 | 5/1988 | Australia .................. | 540/542 |
| 8781692 | 6/1988 | Australia .................. | 546/23 |

OTHER PUBLICATIONS

Unterspann, 1 *European J. Nuclear Medicine* 151 (1976).
Izv. Akad. Nauk SSSR, Ser. Khim (12)2802 (1983) (Chemical Abstract 100:121244).

*Primary Examiner*—Alan L. Rotman
*Attorney, Agent, or Firm*—Kim William Zerby; David L. Suter; Karen F. Clark

[57] ABSTRACT

The present invention relates to novel heterocycle-substituted diphosphonic acids, and the pharmaceutically-acceptable salts and esters thereof, in which the diphosphonate-substituted carbon atom moiety is attached to a carbon atom in a nitrogen-containing six membered ring heterocycle, preferably a piperidine ring. The heterocycle-substituted diphosphonic acid compounds have the general structure:

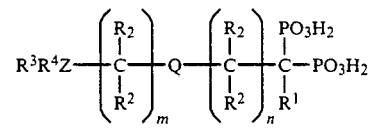

wherein Z is a nitrogen-containing six membered ring heterocycle moiety selected from piperidinyl, diazinyl and triazinyl; m, n and m+n are from 0 to 10; Q is a covalent bond or a moiety selected from oxygen, sulfur or nitrogen; and $R^1$, $R^2$, $R^3$ and $R^4$ are substituent groups.

The present invention further relates to pharmaceutical compositions containing these novel compounds. Finally this invention relates to methods for treating or preventing diseases characterized by abnormal calcium and phosphate metabolism by utilizing a compound or pharmaceutical composition of the present invention.

16 Claims, No Drawings

CERTAIN HETEROCYCLIC SUBSTITUTED DIPHOSPHONATE COMPOUNDS PHARMACEUTICAL COMPOSITIONS, AND METHODS OF TREATING ABNORMAL CALCIUM AND PHOSPHATE METABOLISM

This is a continuation-in-part of prior application Ser. No. 945,068, filed Dec. 19, 1986, now abandoned.

BACKGROUND OF THE INVENTION

This invention relates to novel heterocycle-substituted geminal diphosphonate compounds in which the diphosphonate moiety is attached to a carbon atom in a nitrogen-containing six membered ring heterocycle, preferably a piperidine ring. This invention further relates to pharmaceutical compositions containing these novel compounds. Finally, this invention relates to a method of treating or preventing diseases characterized by abnormal calcium and phosphate metabolism by utilizing a compound or pharmaceutical compositions of the present invention.

A number of pathological conditions which can afflict warm-blooded animals involves abnormal calcium and phosphate metabolism. Such conditions may be divided into two broad categories.

1. Conditions which are characterized by anomalous mobilization of calcium and phosphate leading to general or specific bone loss, or excessively high calcium and phosphate levels in the fluids of the body, such as osteoporosis and Paget's disease. Such conditions are sometimes referred to herein as pathological hard tissue demineralizations.
2. Conditions which cause or result from deposition of calcium and phosphate anomalously in the body, such as arthritis. These conditions are sometimes referred to herein as pathological calcifications.

A variety of polyphosphonic acid derivatives have been proposed for use in the treatment and prophylaxis of diseases involving abnormal calcium and phosphate metabolism. For example, U.S. Pat. No. 3,683,080, issued Aug. 8, 1972 to Francis, discloses compositions containing polyphosphonates, in particular diphosphonates such as ethane-1-hydroxy-1,1-diphosphonic acid ("EHDP"), and their use in inhibiting anomalous deposition and mobilization of calcium and phosphate in animal tissue; U.S. Pat. No. 4,230,700, issued Oct. 28, 1980 to Francis, discloses compositions containing certain diphosphonates, including cycloalkyl-substituted hydroxy ethane diphosphonates, and vitamin D-like compounds for inhibiting mobilization of calcium phosphate in animal tissue; U.S. Pat. No. 4,267,108, issued May 12, 1981 to Blum et al, discloses 2'-pyrrolidine-1-hydroxymethane-1,1-diphosphonic acid said to be useful for treating diseases related to the abnormal deposition or dissolution of difficulty soluble calcium salts in the animal body; European Patent Application Publication No. 100,718, published Feb. 15, 1984 by Sanofi S. A., discloses pyridine-substituted thioalkane diphosphonates said to be useful for treating inflammatory diseases such as arthritis; European Patent Application Publication No. 170,228, published Feb. 5, 1986 by Boehringer Mannheim GmbH, discloses pyridine-substituted longer-chain alkane diphosphonates said to be useful for treating calcium metabolism disorders; and European Patent Application Publication No. 186,405, published July 2, 1986 by Benedict and Perkins, discloses pyridine-substituted diphosphonates said to be useful for treating diseases characterized by abnormal calcium and phosphate metabolism. The disclosures of all these patents and applications are incorporated herein by reference in their entirety.

In addition, Unterspann, *European Journal of Nuclear Medicine*, 1 (3), pp 151-154 (1976), and Unterspann, *Vortragssamml.-Nuklearmed. Symp.* 12th, Meeting Date 1975, pp 241-248 (1976; Klaus Schwartz, Editor) compare N-piperidinyl-methane-diphosphonic acid (a compound which is structurally similar to the compounds of the present invention) with other diphosphonate compounds, including EHDP, for Technetium-99m labelability and suitability for bone scintigraphy. The data obtained from these studies indicate that this compound has less skeleton activity than EHDP. Furthermore, Landeck and Binus, *Stomatol. DDR*, 30 (3), pp 169-175 (1980), apparently used the same compound to investigate the effect of parenteral administration of certain diphosphonates on the size and structure of hamsters' incisors. Little or no effect on the mineralization of the incisors was observed for hamsters treated with this compound.

It has been surprisingly discovered that the heterocycle-substituted diphosphonate compounds of the present invention, which have the diphosphonate moiety attached to a carbon atom in a nitrogen-containing six membered ring heterocycle (preferably a piperidine ring), have potent bone antiresorptive activity. This activity is significantly greater than EHDP. Thus, in spite of the above-noted and much other research into the use of diphosphonates to treat bone-metabolism diseases, there continues to be a need for potent new bone-active agents. It is therefore an object of the present invention to provide new bone-active diphosphonate compounds which are potent bone resorption inhibiting agents. It is a further object of the present invention to provide pharmaceutical compositions useful for the treatment and prophylaxis of abnormal calcium and phosphate metabolism. In addition, it is an object of the present invention to provide methods for treating or preventing diseases characterized by abnormal calcium and phosphate metabolism in humans or lower animals.

These and other objects of the present invention will become apparent from the detailed disclosure of the present invention provided hereinafter.

SUMMARY OF THE INVENTION

The present invention relates to heterocycle-substituted diphosphonic acids, and the pharmaceutically-acceptable salts and esters thereof, in which the diphosphonate-substituted carbon atom moiety is attached to a carbon atom in a nitrogen-containing six membered ring heterocycle, preferably a piperidine ring. These compounds have the general structure:

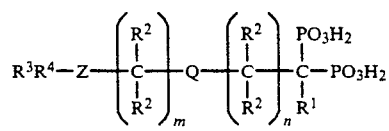

In this general structure, Z is a nitrogen-containing six membered ring heterocycle moiety selected from piperidinyl, diazinyl, and triazinyl (preferably Z is piperidinyl). In addition, m and n and m+n are integers from about 0 to about 10 (preferably m+n=0, 1 or 2); and Q is a covalent bond or a moiety selected from the group consisting of oxygen, sulfur, or nitrogen. Further in this general structure, each $R^1$, $R^2$, $R^3$ and $R^4$ is independently selected from a variety of substituent groups with most preferred $R^1$ being hydrogen, hydroxy and amino; most preferred $R^2$ being hydrogen; and most preferred $R^3$ and $R^4$ being hydrogen and methyl. Finally, in this general structure the Q-containing chain is not attached to the heterocycle ring at the nitrogen atom of the heterocycle ring.

The present invention further relates to pharmaceutical compositions containing a safe and effective amount of a compound of the present invention, and a pharmaceutically-acceptable carrier. Finally, the present invention relates to methods for treating or preventing pathological conditions characterized by abnormal calcium and phosphate metabolism in humans or lower animals. This method comprises administering to a human or lower animal in need of such treatment a safe and effective amount of a compound or composition of the present invention.

DETAILED DESCRIPTION OF THE INVENTION

Heterocycle-substituted diphosphonate compounds

The compounds of the present invention are heterocycle-substituted diphosphonic acids, and the pharmaceutically-acceptable salts and esters thereof, in which the diphosphonic acid-containing carbon atom is linked to a carbon atom in a nitrogen-containing six membered ring heterocycle, preferably a piperidine ring. The linkage from the diphosphonic acid-containing carbon atom to the heterocycle ring may be direct through a covalent bond (preferably a single bond), or by a chain of length of from about 1 to about 10 atoms. If the linkage is via a linking chain, this chain may be all carbon atoms, a nitrogen atom or nitrogen-containing chain, an oxygen atom or oxygen-containing chain, or a sulfur atom or sulfur-containing chain. The carbon and nitrogen atoms in the linking chains may, independently, be unsubstituted or substituted with one or more substituents selected from methyl, ethyl, or propyl. Unsubstituted carbon and nitrogen atoms in the chain are preferred. Also preferred are chains one atom in length, i.e., —CH$_2$—, —NH—, —S—, and —O—.

For the compounds in which a sulfur, nitrogen or oxygen atom in the linking chain is bonded to the heterocycle ring, this sulfur, nitrogen or oxygen atom is preferably bonded to the ring at a carbon atom not bonded directly to the ring's nitrogen atom. For the compounds in which a nitrogen atom in the linking chain is bonded to the heterocycle ring, when this nitrogen atom is bonded to a carbon atom bonded directly to a nitrogen atom in the heterocycle, then these compounds have an ylidene structure (as described more fully hereinafter).

The carbon atom which has the phosphonate groups attached to it may be unsubstituted (i.e., a hydrogen atom), or substituted. Furthermore, the carbon atoms in the heterocycle ring may be unsubstituted or substituted independently with one or more substituents. The nitrogen atom in the heterocycle ring may be unsubstituted or substituted.

Thus, the heterocycle-substituted diphosphonic acids of the present invention, and the pharmaceutically-acceptable salts and esters thereof, are substituted with a nitrogen-containing six membered ring heterocycle and have the general structure:

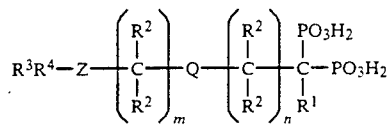

In this general structure, Z is a nitrogen containing six membered ring heterocycle moiety selected from piperidinyl, diazinyl, (e.g., 1,2-diazinyl; 1,3-diazinyl; 1,4-diazinyl (also known as piperazinyl)), and triazinyl (e.g., 1,2,4-triazinyl; 1,3,5-triazinyl); and $R^1$, $R^2$, $R^3$, $R^4$, Q, m and n are as described hereinafter. Preferred Z is selected from piperidinyl; 1,3-diazinyl; and 1,4-diazinyl. Most preferred Z is piperidinyl.

The preferred piperidine-substituted diphosphonic acids, and the pharmaceutically-acceptable salts and esters thereof, according to the present invention have the general structure:

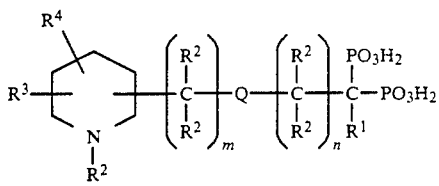

In these general structures, Q is a covalent bond (preferably a single bond) or a moiety selected from oxygen, —NR$^2$—, or sulfur. Further, m and n and m+n are integers from about 0 to about 10, with m+n=0 or 1 preferred (and m=0 and n=0 or 1 more preferred) for Q being oxygen, sulfur, or —NR$^2$—; and with m+n=0, 1, or 2 preferred for Q being a covalent bond. Each $R^2$ moiety is independently selected from hydrogen, methyl, ethyl and propyl. Preferred is each $R^2$ being hydrogen or methyl, and most preferred is all $R^2$ being hydrogen.

The $R^1$ moiety is selected from hydrogen; halogen; alkyl having from about 1 to about 6 carbon atoms; phenyl; benzyl; hydroxy, and the ester thereof derived from a carboxylic acid having from about 1 to about 6 carbon atoms; unsubstituted amino, and the amide thereof derived from a carboxylic acid having from about 1 to about 6 carbon atoms; amino substituted with one alkyl group having from about 1 to about 6 carbon atoms, and the amide thereof derived from a carboxylic acid having from about 1 to about 6 carbon atoms; amino substituted independently with two alkyl groups having from about 1 to about 6 carbon atoms; ammonium substituted independently with three alkyl groups having from about 1 to about 6 carbon atoms; —CO$_2$H, the pharmaceutically-acceptable salts thereof, the ester thereof derived from alcohols having from about 1 to about 6 carbon atoms, the unsubstituted amide thereof, and the amide thereof substituted with one or two alkyl groups having from about 1 to about 6 carbon atoms; and combinations thereof.

However, when n=0 and Q is oxygen, sulfur or nitrogen, then $R^1$ is selected from hydrogen; alkyl having from about 1 to about 6 carbon atoms; phenyl; benzyl; —CO$_2$H, the pharmaceutically-acceptable salts thereof, the ester thereof derived from alcohols having from about 1 to about 6 carbon atoms, the unsubstituted amide thereof, and the amide thereof substituted with one or two alkyl groups having from about 1 to about 6 carbon atoms; and combinations thereof.

Preferred $R^1$ is selected from hydrogen, chloro, methyl, ethyl, hydroxy, unsubstituted amino, (N-methyl)amino, (N,N-dimethyl)amino, —$CO_2H$ and the pharmaceutically-acceptable salts thereof, —$CO_2CH_3$, and —$CONH_2$. More preferred $R^1$ is selected from hydrogen, methyl, chloro, amino, and hydroxy. Most preferred $R^1$ is hydrogen, hydroxy, or amino.

The heterocycle ring in the compounds of the present invention may be unsubstituted or substituted on the carbon atoms independently with one or more substituents ($R^3$ and $R^4$). Except for the ylidene structures described hereinafter, the heterocycle ring is fully saturated and the $R^3$ and $R^4$ substituents may be bonded to any of the carbon atoms in the heterocycle ring. The $R^3$ and $R^4$ groups may be on the same carbon atom, or on different carbon atoms of the heterocycle. Therefore, in the hereinbefore general structure all the available bonds to the carbon atoms in the heterocycle ring are attached to $R^3$ and $R^4$ substituents, preferably hydrogen.

Thus, the $R^3$ and $R^4$ groups are substituents, on one or more carbon atoms of the heterocycle, independently selected from hydrogen; halogen; alkyl having from about 1 to about 3 carbon atoms; unsubstituted amino, and the amide thereof derived from a carboxylic acid having from about 1 to about 3 carbon atoms; amino substituted with one alkyl group having from about 1 to about 3 carbon atoms, and the amide thereof derived from a carboxylic acid having from about 1 to about 3 carbon atoms; amino substituted independently with two alkyl groups having from about 1 to about 3 carbon atoms; ammonium substituted independently with three alkyl groups having from about 1 to about 3 carbon atoms; hydroxy, or the ester thereof derived from a carboxylic acid having from about 1 to about 3 carbon atoms; ether having from about 1 to about 3 carbon atoms; —$CO_2H$, the pharmaceutically-acceptable salts thereof, the ester thereof derived from alcohols having from about 1 to about 3 carbon atoms, the unsubstituted amide thereof, and the amide thereof substituted with one or two alkyl groups having from about 1 to about 3 carbon atoms; nitro; and combinations thereof.

Preferred $R^3$ and $R^4$ substituents are independently selected from hydrogen, methyl, ethyl, hydroxy unsubstituted amino, (N-methyl)amino, (N,N-dimethyl)amino, chloro, methoxy, ethoxy, nitro, —$CO_2H$ and the pharmaceutically-acceptable salts thereof, —$CO_2CH_3$, $CONH_2$, and combinations thereof. More preferred $R^3$ and $R^4$ substituents are independently selected from hydrogen, methyl, amino, chloro, methoxy, hydroxy and combinations thereof. Most preferred $R^3$ and $R^4$ substituents are independently selected from hydrogen and methyl.

Furthermore in the hereinbefore general structures, when m=0 and Q is oxygen, nitrogen or sulfur, then the bonding of the Q moiety to the heterocycle ring is preferably limited as follows. The Q moiety is bonded to the heterocycle ring at a carbon atom not bonded directly to a nitrogen atom in the heterocycle ring (e.g., the 3, 4, or 5 positions of a piperidine ring when counting the nitrogen atom as the 1 position of the ring), except that when Q is nitrogen then Q may also be bonded to the heterocycle ring by an ylidene structure. A compound of the present invention having an ylidene structure comprises a N=C—N chemical bonding as part of the heterocycle ring.

For the preferred piperidine-substituted diphosphonic acid compounds of the present invention, the piperidinylidene structure may be either one of the following general structures:

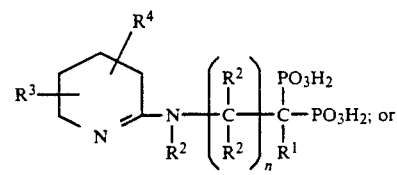

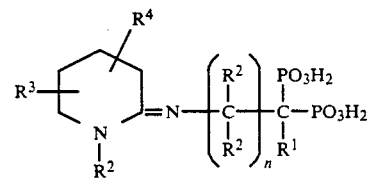

When the N—$R^2$ moiety is N—H, these structures are probably in equilibrium.

In addition, for the heterocycle-substituted diphosphonic acids which have more than one nitrogen atom, such as the diazinyl-substituted diphosphonic acids, the ylidene structure may have three nitrogen atoms bonded to the same carbon atom. Thus, these compounds may have ylidene structures such as the ylidene structure for N-(2'-(1',3'-diazinylidene))-aminomethane diphosphonate:

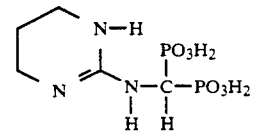

This compound is probably an equilibrium mixture of the above structure, and the other two structures in which the N to C double bond is possible.

More specifically, the piperidine-substituted diphosphonic acids, and the pharmaceutically-acceptable salts and esters thereof, of the present invention have the general structures:

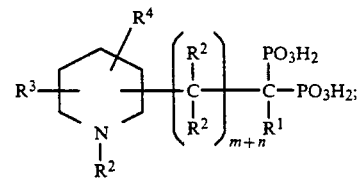

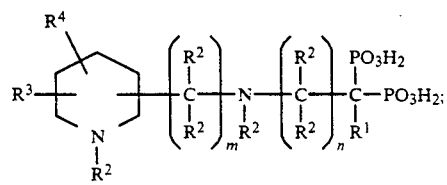

-continued

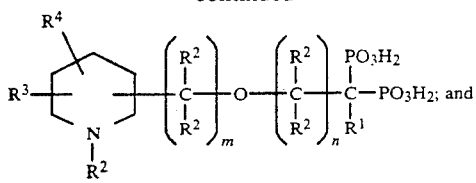

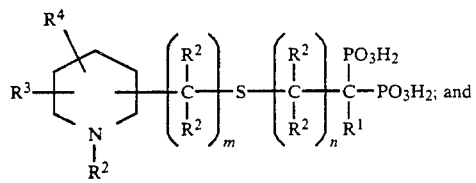

wherein m, n, m+n, $R^1$, $R^2$, $R^3$ and $R^4$ are as described hereinbefore.

Preferred piperidine-substituted diphosphonic acids, and the pharmaceutically acceptable salts and esters thereof, of the present invention have the general structures:

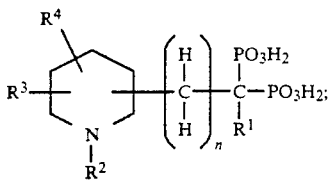

wherein n=0, 1, or 2, with preferred being n=0 or 1, and most preferred is n=1; $R^1$ is hydrogen, methyl, chloro, amino, or hydroxy; $R^2$ is hydrogen or methyl, with preferred $R^2$ being hydrogen; and $R^3$ and $R^4$ are substituents independently selected from hydrogen, methyl, amino, chloro, methoxy, hydroxy, and combinations thereof, with most preferred $R^3$ being hydrogen or methyl;

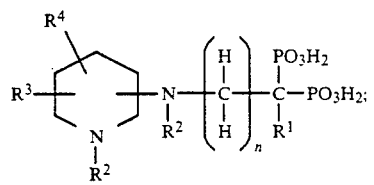

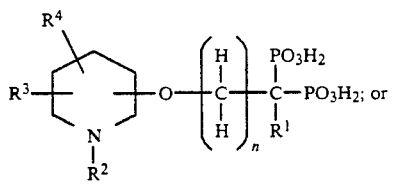

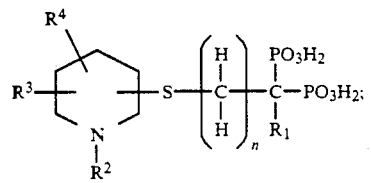

wherein for the three preceding structures n=0 or 1; $R^1$ is hydrogen, methyl, chloro, amino, or hydroxy when n=1, and $R^1$ is hydrogen or methyl when n=0, with n=0 and $R^1$ being hydrogen most preferred; $R^2$ is hydrogen or, methyl, with preferred $R^2$ being hydrogen; and $R^3$ and $R^4$ are substituents independently selected from the group consisting of hydrogen, methyl, amino, chloro, methoxy, hydroxy, and combinations thereof, with most preferred $R^3$ and $R^4$ being hydrogen or methyl.

The preferred piperidinylidene structures for the compounds of the present invention are:

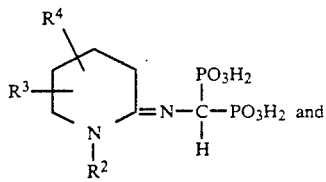

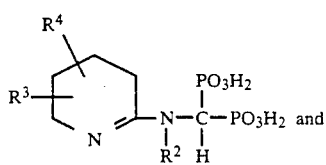

wherein $R^2$ is selected from hydrogen or methyl, with preferred $R^2$ being hydrogen; and $R^3$ and $R^4$ are substituents independently selected from the group consisting of hydrogen, methyl, amino, chloro, methoxy, hydroxy, and combinations thereof, with most preferred $R^3$ and $R^4$ being hydrogen or methyl.

The term "alkyl", as used herein, means carbon-containing chains which may be straight or branched, and which may be saturated, monounsaturated, or polyunsaturated. Preferred are saturated alkyl groups. Further, while it is preferred that the alkyl, phenyl, and benzyl substituent groups described hereinbefore be unsubstituted, these groups themselves may be substituted with a variety of substituents (e.g.: methyl, ethyl, propyl, substituted or unsubstituted amino, carboxy, hydroxy, methoxy, ethoxy, halogen) and still be considered within the scope of the present invention.

By "pharmaceutically-acceptable salts and esters" as used herein is meant hydrolyzable esters and salts of the diphosphonate compounds which have the same general pharmacological properties as the acid form from which they are derived, and which are acceptable from a toxicity viewpoint. Pharmaceutically-acceptable salts include alkali metal (sodium and potassium), alkaline earth metal (calcium and magnesium), non-toxic heavy metal (stannous and indium), and ammonium and low molecular weight substituted ammonium (mono-, di- and triethanolamine) salts. Preferred compounds are the sodium, potassium, and ammonium salts.

Specific examples of compounds of the present invention include:
(2'-piperidinyl)-methane diphosphonic acid;
(3'-piperidinyl)-methane diphosphonic acid;
(4'-piperidinyl)-methane diphosphonic acid;
2-(2'-piperidinyl)-ethane-1,1-diphosphonic acid;
2-(3'-piperidinyl)-ethane-1,1-diphosphonic acid;
2-(4'-piperidinyl)-ethane-1,1-diphosphonic acid;
2-(2'-piperidinyl)-1-hydroxy-ethane-1,1-diphosphonic acid;
2-(3'-piperidinyl)-1-hydroxy-ethane-1,1-diphosphonic acid;
2-(4'-piperidinyl)-1-hydroxy-ethane-1,1-diphosphonic acid;

2-(2'-(3'-methyl)-piperidinyl)-ethane-1,1-diphosphonic acid;
2-(2'-(5'-methyl)-piperidinyl)-ethane-1,1-diphosphonic acid;
2-(2'-(3'-methyl)-piperidinyl)-1-hydroxy-ethane-1,1-diphosphonic acid;
3-(2'-piperidinyl)-propane-1,1-diphosphonic acid;
3-(3'-piperidinyl)-propane-1,1-diphosphonic acid;
3-(4'-piperidinyl)-propane-1,1-diphosphonic acid;
3-(2'-piperidinyl)-1-hydroxy-propane-1,1-diphosphonic acid;
3-(3'-piperidinyl)-1-hydroxy-propane-1,1-diphosphonic acid;
3-(4'-piperidinyl)-1-hydroxy-propane-1,1-diphosphonic acid;
3-(2'-piperidinyl)-propane-2,2-diphosphonic acid;
3-(3'-piperidinyl)-propane-2,2-diphosphonic acid;
3-(4'-piperidinyl)-propane-2,2-diphosphonic acid;
2-(2'-(N-methyl)-piperidinyl)-1-hydroxy-ethane-1,1-diphosphonic acid;
2-(2'-piperidinyl)-1-amino-ethane-1,1-diphosphonic acid;
2-(3'-piperidinyl)-1-amino-ethane-1,1-diphosphonic acid;
2-(4'-piperidinyl)-1-amino-ethane-1,1-diphosphonic acid;
2-(2'-(3'-methyl)-piperidinyl)-1-amino-ethane-1,1-diphosphonic acid;
2-(2'-piperidinyl)-1-hydroxy-propane-1,1-diphosphonic acid;
3-(2'-piperidinyl)-propionic acid-2,2-diphosphonic acid;
2-(2'-piperidinyl)-1-(N-methyl)amino-ethane-1,1-diphosphonic acid;
4-(2'-piperidinyl)-1-hydroxy-butane-1,1-diphosphonic acid;
2-(2'-(5'-amino)-piperidinyl)-1-hydroxy-ethane-1,1-diphosphonic acid;
2-(2'-(3'-ethyl)-piperidinyl)-1-hydroxy-ethane-1,1-diphosphonic acid;
2-(2'-(3'-carboxy)-piperidinyl)-1-hydroxy-ethane-1,1-diphosphonic acid;
2-(2'-(5'-carboxy)-piperidinyl)-1-hydroxy-ethane-1,1-diphosphonic acid;
2-(2'-(1',4'-diazinyl))-ethane-1,1-diphosphonic acid;
2-(2'-(1',4'-diazinyl))-1-hydroxy-ethane-1,1-diphosphonic acid;
2-(2'-(1',3'-diazinyl))-ethane-1,1-diphosphonic acid;
2-(3'-(1',2'-diazinyl))-ethane-1,1-diphosphonic acid;
N-(2'-piperidinylidene)-amino-methane diphosphonic acid;
N-(3'-piperidinyl)-amino-methane diphosphonic acid;
N-(4'-piperidinyl)-amino-methane diphosphonic acid;
N-(2'-(3'-methyl)-piperidinylidene)-amino-methane diphosphonic acid;
N-(2'-(5'-methyl)-piperidinylidene)-amino-methane diphosphonic acid;
2-(N-(2'-piperidinylidene)-amino)-ethane-1,1-diphosphonic acid;
1-(N-(2'-piperidinylidene)-amino)-ethane-1,1-diphosphonic acid;
N-(2'-(1',3'-diazinylidene))-aminomethane diphosphonic acid;
N-(2'-(1',4'-diazinylidene))-aminomethane diphosphonic acid;
N-(2'-(1',3',5'-triazinylidene))-aminomethane diphosphonic acid;
N-(4'-(1',2'-diazinyl))-aminomethane diphosphonic acid;
O-(3'-piperidinyl)-oxamethane diphosphonic acid;
O-(4'-piperidinyl)-oxamethane diphosphonic acid;
2-(O-(3'-piperidinyl)-oxa)-ethane-1,1-diphosphonic acid;
1-(O-(3'-piperidinyl)-oxa)-ethane-1,1-diphosphonic acid;
O-(4'-(1',2'-diazinyl))-oxamethane diphosphonic acid;
S-(3'-piperidinyl)-thiomethane diphosphonic acid;
S-(4'-piperidinyl)-thiomethane diphosphonic acid;
2-(S-(3'-piperidinyl)-thio)-ethane-1,1-diphosphonic acid;
1-(S-(3'-piperidinyl)-thio)-ethane-1,1-diphosphonic acid;
S-(4'-(1',2'-diazinyl))-thiomethane diphosphonic acid;
and the pharmaceutically-acceptable salts and esters thereof.

Preferred compounds of the present invention include:
2-(2'-piperidinyl)-ethane-1,1-diphosphonic acid;
2-(3'-piperidinyl)-ethane-1,1-diphosphonic acid;
2-(4'-piperidinyl)-ethane-1,1-diphosphonic acid;
2-(2'-piperidinyl)-1-hydroxy-ethane-1,1-diphosphonic acid;
2-(3'-piperidinyl)-1-hydroxy-ethane-1,1-diphosphonic acid;
2-(4'-piperidinyl)-1-hydroxy-ethane-1,1-diphosphonic acid;
2-(2'-(3'-methyl)piperidinyl)-ethane-1,1-diphosphonic acid;
2-(2'-(5'-methyl)piperidinyl)-ethane-1,1-diphosphonic acid;
2-(2'-(3'-methyl)piperidinyl)-1-hydroxy-ethane-1,1-diphosphonic acid;
3-(2'-piperidinyl)-1-hydroxy-propane-1,1-diphosphonic acid;
3-(3'-piperidinyl)-1-hydroxy-propane-1,1-diphosphonic acid;
N-(2'-(3'-methyl)-piperidinylidene)-amino-methane diphosphonic acid;
N-(2'-(1',3'-diazinylidene))-aminomethane diphosphonic acid;
and the pharmaceutically-acceptable salts and esters thereof.

Most preferred compounds of the present invention include:
2-(2'-piperidinyl)-ethane-1,1-diphosphonic acid;
2-(3'-piperidinyl)-ethane-1,1-diphosphonic acid;
2-(2'-piperidinyl)-1-hydroxy-ethane-1,1-diphosphonic acid;
2-(3'-piperidinyl)-1-hydroxy-ethane-1,1-diphosphonic acid;
N-(2'-(3'-methyl)-piperidinylidene)-amino-methane diphosphonic acid;
N-(2'-(1',3'-diazinylidene))-aminomethane diphosphonic acid;
and the pharmaceutically-acceptable salts and esters thereof.

In order to determine and assess pharmacological activity, testing of the diphosphonate compounds in animals is carried out using various assays known to those skilled in the art. Thus, the in vivo bone antiresorptive activity may be conveniently demonstrated using an assay designed to test the ability of these compounds to inhibit the resorption of bone, which bone resorption is characteristic of abnormal calcium and phosphate metabolism. Examples of such known tests include the thyroparathyroidectomized ("TPTX") rat model and the Schenk model. Another useful art-known test is the adjuvant arthritis test. Also useful is the in vitro hydroxyapatite crystal growth inhibition test. These and other appropriate tests for pharmacological activity are disclosed and/or referred to in Shinoda et al., *Calcified Tissue International*, 35, pp 87–99 (1983); Schenk et al., *Calcified Tissue Research*, 11, pp 196–214 (1973); Russell et al., *Calcified Tissue Research*, 6, pp 183–196 (1970); Muhlbauer and Fleisch, *Mineral Electrolyte Metab.*, 5, pp 296–303 (1981); Nancollas et al., *Oral Biol.*, 15, 731 (1970); U.S. Pat. No. 3,683,080, to Francis, Issued Aug. 8, 1972; U.S. Pat. No. 4,134,969, to Schmidt-Dunker, Issued Jan. 16, 1979; and EPO Patent Application Publication No. 189,662, published Aug. 6, 1986; the disclosures of all these articles and patent specifications being incorporated herein by reference in their entirety. Certain of these tests for pharmacological activity are also described in more detail in the Examples provided hereinafter.

In addition to being useful for treating or preventing pathological conditions characterized by abnormal calcium or phosphate metabolism, the compounds of the present invention may have other uses. For example, the compounds of the present invention are believed to be useful as bone scanning agents after labeling with 99m-Technetium. In addition, the compounds of the present invention are useful as sequestering agents for polyvalent metal ions, particularly di- and tri-valent metal ions (e.g. calcium and magnesium). Thus, the compounds of the present invention are useful as builders in detergents and cleansers, or for treating water. They are also useful as stabilizers for percompounds. In addition, they may be useful in preventing the formation of tartar (i.e., calculus) and/or plaque on teeth. Finally, the compounds of the present invention may be useful as herbicides which are non-toxic to animals.

The diphosphonate compounds to be included in the pharmaceutical compositions of the present invention can be made using synthetic methods known in the art and simple hydrogenation techniques. For example, those methods disclosed in Japanese Patent Application No. 80/98,193, published July 25, 1980 by Nissan Kygaku Kagyo K. K.; Japanese Patent Application No. 80/98,105, published July 25, 1980 by Nissan Chemical Industries; West German Patent 2,831,578, published Feb. 1, 1979, by Fumio; Ploger et al., *Z. Anorg. Allg. Chem.*, 389, 119 (1972); U.S. Pat. No. 4,267,108, issued May 12, 1981 to Blum et al.; European Patent Application Publication No. 100,718, published Feb. 15, 1984 by Sanofi S. A.; European Patent Application Publication No. 170,228, published Feb. 5, 1986 by Boehringer Mannheim GmbH; and European Patent Application Publication No. 186,405, published July 2, 1986 by Benedict and Perkins; the disclosures of all these being incorporated herein by reference in their entirety. Synthesis procedures are also exemplified by the Examples provided hereinafter.

Compounds of the present invention may comprise from about 0.1% to about 99.9% by weight of the pharmaceutical compositions of the present invention. Preferably the compounds of the present invention comprise from about 20% to about 80% by weight of the pharmaceutical compositions of the present invention.

Pharmaceutically-acceptable Carrier

In addition to the heterocycle-substituted diphosphonate compound as described hereinbefore, the pharmaceutical compositions of the present invention essentially contain a pharmaceutically-acceptable carrier. By "pharmaceutically-acceptable carrier" as used herein, is meant one or more compatible solid or liquid filler diluents or encapsulating substances. By "compatible" as used herein is meant that the components of the composition are capable of being commingled without interacting in a manner which would substantially decrease the pharmaceutical efficacy of the total composition under ordinary use situations.

Some examples of substances which can serve as pharmaceutical carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin, talc; stearic acid; magnesium stearate; vegetable oils, such as peanut oil, cottonseed oil, sesame oil, olive oil, corn oil and oil of theobroma; polyols such as propylene glycol, glycerin, sorbitol, mannitol, and polyethylene glycol; sugar; alginic acid; pyrogen-free water; isotonic saline; and phosphate buffer solutions, as well as other non-toxic compatible substances used in pharmaceutical formulations. Wetting agents and lubricants such as sodium lauryl sulfate, as well as coloring agents, flavoring agents, lubricants, excipients, tableting agents, stabilizers, anti-oxidants and preservatives, can also be present. Other compatible pharmaceutical additives and actives (e.g., vitamin D or vitamin D metabolites, and mineral supplements) may be included in the pharmaceutical compositions of the present invention.

The choice of a pharmaceutical carrier to be used in conjunction with the diphosphonates of the present compositions is basically determined by the way the diphosphonate is to be administered. If the compound is to be injected, the preferred pharmaceutical carrier is sterile, physiological saline, the pH of which has been adjusted to about 7.4. However, the preferred mode of administering the diphosphonates of the present invention is orally, and the preferred unit dosage form is therefore tablets, capsules and the like, comprising from about 0.1 mg P to about 600 mg P of the diphosphonic acid compounds described herein. Pharmaceutical carriers suitable for the preparation of unit dosage forms for oral administration are well known in the art. Their selection will depend on secondary considerations like taste, cost, and shelf stability, which are not critical for the purposes of the present invention, and can be made without difficulty by a person skilled in the art.

The term "mg P", as used herein, means the weight of the phosphorous atoms present in an amount of a diphosphonic acid compound of the present invention. This unit is used to standardize the amount of the diphosphonic acid compounds of the present invention to be used in the pharmaceutical compositions and methods of the present inventions. For example, 2-(2'-piperidinyl)-ethane-1,1-diphosphonic acid has a molecular weight of 273 g/mole, of which 22.7% (62 g/mole) is due to the two phosphorous atoms present in this molecule. One milligram of this compound is therefore calculated to have 0.227 mg P (1 mg $\times$ 22.7%). Thus, to prepare a pharmaceutical composition containing 0.227 mg P of this compound, the composition should contain 1 mg of the compound; and to dose 0.227 mg P/kg of this compound to a 50 kg patient, the patient would be dosed with 50 mg of this compound.

The pharmaceutically-acceptable carrier employed in conjunction with the diphosphonates of the present invention is used at a concentration sufficient to provide a practical size to dosage relationship. Preferably, the pharmaceutically-acceptable carriers, in total, may comprise from about 0.1% to about 99.9% by weight of the total composition and more preferably from about 20% to about 80%.

Method for Treating or Preventing Diseases Characterized by Abnormal Calcium and Phosphate Metabolism Another aspect of the present invention is methods for treating or preventing diseases characterized by abnormal calcium and phosphate metabolism. Such methods comprise administering to a human or lower animal in need of such treatment a safe and effective amount of diphosphonate compound of the present invention.

The preferred mode of administration is oral, but other known methods of administration are contemplated as well, e.g., dermatomucosally (for example, dermally, rectally and the like) and parenterally (for example, by subcutaneous injection, intramuscular injection, intra-articular injection, intravenous injection and the like). Inhalation is also included. Thus, specific modes of administration include, without limitation, oral, transdermal, mucosal, sublingual, intramuscular, intravenous, intraperitoneal, and subcutaneous administration, as well as topical application.

The term "abnormal calcium and phosphate metabolism", as used herein, means (1) conditions which are characterized by anomalous mobilization of calcium and phosphate leading to general or specific bone loss, or excessively high calcium and phosphate levels in the fluids of the body; and (2) conditions which cause or result from deposition of calcium and phosphate anomalously in the body. The first category includes, but is not limited to, osteoporosis, Paget's disease, hyperparathyroidism, hypercalcemia of malignancy, heterotopic ossification, and osteolytic bone metastases. The second category includes, but is not limited to, myositis ossificans progressiva, calcinosis universalis, and such afflictions as arthritis, osteoarthritis, neuritis, bursitis, tendonitis and other inflammatory conditions which predispose involved tissue to deposition of calcium and phosphate.

The terms "person at risk" and "person in need of such treatment", as used herein, mean any human or lower animal which suffers a significant risk of abnormal calcium and phosphate metabolism if left untreated, and any human or lower animal diagnosed as being afflicted with abnormal calcium and phosphate metabolism. For example, postmenopausal women; persons undergoing certain steroid therapy; persons on certain anti-convulsant drugs; persons diagnosed as having Paget's disease, hyperparathyroidism, hypercalcemia of malignancy, or osteolytic bone metastases; persons diagnosed as suffering from one or more of the various forms of osteoporosis; persons belonging to a population group known to have a significantly higher than average chance of developing osteoporosis, e.g., postmenopausal women, men over age 65, and persons being treated with drugs known to cause osteopetrosis as a side effect; persons diagnosed as suffering from myositis ossificans progressiva or calcinosis universalis; and persons afflicted with arthritis, osteoarthritis, neuritis, bursitis, tendonitis and other inflammatory conditions which predispose involved tissue to deposition of calcium and phosphate.

The phrase "safe and effective amount", as used herein, means an amount of a compound or composition of the present invention high enough to significantly positively modify the condition to be treated, but low enough to avoid serious side effects (at a reasonable benefit/risk ratio), within the scope of sound medical judgment. The safe and effective amount of diphosphonate compounds of the present invention will vary with the particular condition being treated, the age and physical condition of the patient being treated, the severity of the condition, the duration of the treatment, the nature of concurrent therapy, the specific diphosphonate employed, the particular pharmaceutically-acceptable carrier utilized, and like factors within the knowledge and expertise of the attending physician. However, single dosages can range from about 0.01 mg P to about 3500 mg P, or from about 0.0002 to about 70 mg P/kg of body weight (based on a body weight of 50 kg). Preferred single dosages are from about 1 mg P to about 600 mg P, or from about 0.02 to about 12 mg P/kg of body weight (based on a body weight of 50 kg). Up to about four single dosages per day may be administered. Daily dosages greater than about 500 mg P/kg are not required to produce the desired effect and may produce undesirable side effects. The higher dosages within this range are, of course, required in the case of oral administration because of limited absorption.

The following Examples further describe and demonstrate the preferred embodiments within the scope of the present invention. The Examples are given solely for the purpose of illustration, and are not to be construed as limitations of the present invention since many variations thereof are possible without departing from its spirit and scope.

EXAMPLE 1

Synthesis of 2-(2'-piperidinyl)-ethane diphosphonic acid monosodium salt.

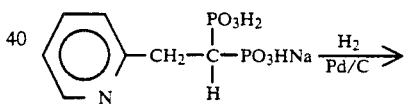

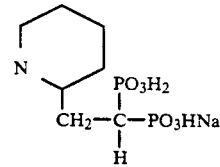

2-(2'-pyridyl)-ethane diphosphonic acid sodium salt (10.03 g; which is prepared as described in European Patent Application Publication No. 186,405) is dissolved in 125 ml of distilled H$_2$O in a 500 ml Parr hydrogenation bottle. Ten percent palladium on activated carbon (0.75 g) is added to this solution. The mixture is then hydrogenated at room temperature (40 psi) for 2 days. The solution is filtered, 0.50 g 10% Pd/C is added to the filtrate, and this mixture is hydrogenated for another 2 days under the same conditions. The solution is again filtered, and the filtrate is concentrated on a rotary evaporator to approximately 25 ml. While heating this liquid, 25 ml of EtOH is added. The solution is then refrigerated overnight. The crude product oils out, and the solvent is decanted off. This oil is concentrated on a rotary evaporator, and then placed on a vacuum pump for 1 day. The resultant solid is ground with a mortar and pestle, and then dried again under vacuum overnight to give 6.5 g of product. After further drying, titration demonstrates 100% purity. $^{31}$P NMR (D$_2$O): 19.18 (s). $^{13}$C NMR (D$_2$O): 24.2 (s); 24.4 (s); 31.2 (s); 32.4 (s); 38.7 (t, J=17 Hz); 47.1 (s) and 59.3 ppm (s); m.p. 350° C.(dec.). Anal. Calcd. for C$_7$H$_{16}$NO$_6$P$_2$Na: C, 28.49; H, 5.46; N, 4.75; Found: C, 27.99; H, 5.52; N, 4.51.

EXAMPLE 2

Synthesis of 2-(3'-piperidinyl)-1-hydroxy-ethane diphosphonic acid monosodium salt

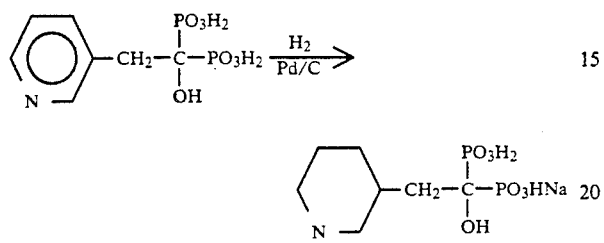

2-(3'-pyridyl)-1-hydroxy-ethane diphosphonic acid (2.0 g; 0.0071 moles; which is prepared as described in European Patent Application Publication No. 186,405) is added to 50 ml of water and the pH is adjusted to pH=6 with 50% NaOH. This solution is placed in a 500 ml Parr hydrogenation bottle and approximately 1 g of 10% Pd/C catalyst is added. The Parr bottle is placed on a Parr hydrogenator apparatus and pressurized to 45 psi of H$_2$ gas. After 4 hr., more catalyst is added and the pressure is brought back up to 45 psi and allowed to react overnight. The completed reaction is verified by $^{31}$P NMR. After hydrogenating, the solution is filtered over celite, washed with water and evaporated down to a clear oil. Ethanol is added (30 ml) to the oil and the mixtures is gently refluxed for 1 hr. to convert the oil to a powdery white precipitate. This solid is filtered and washed with ethanol to yield the product. $^{31}$P NMR (D$_2$O; pH=12): 20.10 ppm (s, decoupled; dd, coupled, J=12 Hz). $^1$H NMR (D$_2$O; pH=12): 3.56 to 1.08 ppm (m). $^{13}$C NMR (D$_2$O; pH=12): 80.757 (t, J=134 Hz), 56.042, 48.347, 42.822, 36.198, 35.7, and 28.823 ppm.

EXAMPLE 3

Synthesis of N-(2'-(3'-methyl)-piperidinylidene)-amino-methane diphosphonic acid monosodium salt

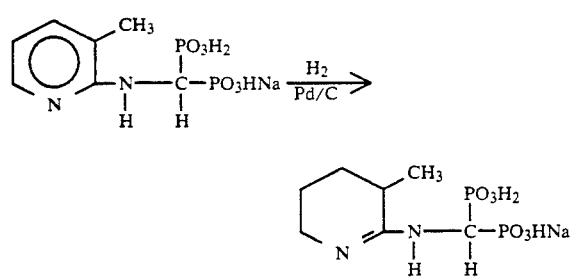

N-(2'-(3'-methyl)pyridyl)-amino-methane diphosphonic acid monosodium salt (5.0 g; which is prepared as described in European Patent Application Publication No. 186,405) is dissolved in 100 ml of distilled H$_2$O in a 500 mL Parr hydrogenation bottle. Ten percent palladium on activated carbon (2.0 g) is added to this solution. The mixture is hydrogenated at room temperature (48 psi) for 12 hr. The solution is filtered and concentrated on a rotary evaporator to yield 3.2 g of desired product. $^{31}$P NMR (D$_2$O): 10.9 ppm (AB q; J=13.20). $^{13}$C NMR (D$_2$O; pH=5): 169.9, 53.8 (t, J=128 Hz), 44.5, 33.8, 28.2, 20.9, and 20.0 ppm.

EXAMPLE 4

Thyroparathyroidectomized (TPTX) Rat Model

The compounds are evaluated for in vivo bone resportion inhibition potency by an animal model system known as the thyroparathyroidectomized (TPTX) rat model. The general principles of this model system are disclosed in Russell et al., *Calcif. Tissue Research*, 6, 183-196 (1970), and in Muhlbauer and Fleisch, *Mineral Electrolyte Metab.*, 5, 296-303 (1981), the disclosures of which are incorporated herein by reference. The basic biochemical concept of the TPTX system is inhibition of the parathyroid hormone (PTH)-induced rise in serum total and ionized calcium levels by the respective bone active polyphosphonates.

(a) Materials

Low calcium and low phosphorous diets used are prepared by Teklad$^R$ Test Diets (Harlan Industries, Madison, Wis. 53711) in a pellet form of approximately 0.18% calcium and 0.22% phosphorous. The diets contain all the essential vitamins and minerals required for the rat, with the exception of calcium and phosphorous. The calcium and phosphorous levels of the pellets are verified analytically.

PTH is acquired as a powdered bovine extract (Sigma Chemical Co., P.O. Box 14508, St. Louis, Mo., order #P-4410). PTH is prepared in 0.9% saline such that the final concentration is 100 μg PTH/ml, or approximately 200 U.S.P. units/ml. All solutions are filtered through a #4 Whatman Filter Paper and refiltered through a 0.45 μm Metricel ® filter.

(b) Dose Solutions and Dosing Procedure

All solutions of compounds to be tested for bone resorption inhibition potency are prepared for subcutaneous injection in 0.9% normal saline and adjusted to pH 7.4 using NaOH and/or HCl. Dose solution calculation is made by considering the mass of powder (based on molecular weight, hydration) of the active material in mg/kg (body weight) that corresponds to mg P/kg. Concentrations are based on dosing 0.2 ml/100 grams of body weight. Typically, all compounds are administered at 0.01, 0.1, and 1.0 mg P/kg/day for 4 days in order to determine the lowest effective dose ("LED"). Where necessary the test is repeated, whereby the animals are administered with 0.5 LED in order to refine the determination of LED. Adjustments in dosage based on changes in body weight are made on a daily basis.

(c) Animals

In this study 50 male Wistar rats weighing approximately 150-160 grams are thyroparathyroidectomized surgically by the breeder (Charles River Breeding Laboratories). All rats are double housed on arrival in suspended cages with Purina Laboratory Rodent Chow ® and tap water ad libitum. After acclimation to the laboratory environment for 3-5 days, the rats are placed on a low calcium, low phosphorous (0.18%/0.22%) diet (Teklad ®) and given 2% (W/V) calcium gluconate supplemented deionized water via water bottles.

(d) Method

On day three of low calcium diet, all rats are weighed. On day four, all rats are anesthetized with Ketaset ® (Ketamine Hydrochloride, 100 mg/ml, Bristol Myers), 0.10 ml/rat, and then bled from the retroorbital venous plexus for serum total calcium analysis using Flame Atomic Absorption (FAA) or Nova 7+7 Automated Calcium Analyzer. All rats weighing less than 150 grams are eliminated from the study. Animals are then randomized statistically such that the mean total serum calcium for each group is the same. Only rats deemed hypocalcemic (total serum calcium ≦ 8.0 mg/dl) are placed in study groups comprising six animals per group.

Treatments with the various experimental compounds commence on day 6 and last through day 9 of the study. Dose solutions are prepared to be given at a constant rate of 0.2 ml/100 grams of body weight subcutaneously in the vental skin flap where the hind leg meets the torso. All rats are weighed and dosed daily. A 25 gauge ⅝" needle is used to administer drug, alternating right and left dose sites daily. On day 8, animals are changed to deionized, distilled water via water bottles. On day 9 all rats are fasted in the afternoon at approximately 4:00 P.M. On day 10 of study no treatment is given. In the morning a 800 μl sample of whole blood is collected from each rat in Microtainer (B-D#5060) serum separator tubes for serum total and ionized calcium (FAA or Nova 7+7). Immediately following blood collection all rats are weighed and injected with bovin parathyroid hormone subcutaneously at a rate of 35 μg PTH per 100 grams of body weight. Blood sampling for total and ionized calcium is repeated three and one-half hours post-PTH injection.

All pre- and post-PTH total and ionized calciums from the treatment groups are statistically analyzed for significance compared to PTH alone (control) using Student's t-test, analysis of variance, and their non-parametric equivalents. The post minus pre-change and % change are also determined on calcium levels and pre-drug vs post-drug body weights.

The physiological effect of the PTH challenge is a rise in serum calcium level, with peak activity observed at three to four hours. Since the hormonal and dietary controls of calcium metabolism are minimized in the TPTX model, an observed increase in serum calcium level is presumably the result of resorption of bone material. Since polyphosphonates tend to inhibit resorption of bone materials, the animals pretreated with polyphosphonate show a rise in serum calcium level after PTH challenge which is less than that found in control animals which have been treated with saline vehicle instead. The lowest dose at which the polyphosphonate is capable of inhibiting bone resorption, as evidenced by a decreased rise in serum calcium upon PTH challenge, is a measure of the bone resorption inhibition potency of the polyphosphonate. The LED values of the bone resorption inhibition potency of representative compounds as determined by the TPTX rat model are presented in Table 1. The data in Table 1 show that the diphosphonic acid compounds of the present invention are potent bone resorption inhibiting agents.

TABLE 1

| Diphosphonate Compound | Lowest Effective (Antiresorptive) Dose-TPTX TPTX (mg P/kg) |
| --- | --- |
| EHDP[1] | 1.0 |
| APD[2] | 0.1 |
| Cl₂MDP[3] | 1.0 |
| 2-(2'-piperidinyl)-EDP*[4] | 0.01 |
| 2-(2'-piperidinyl)-1-hydroxy-EDP*[4] | 0.001 |
| 2-(3'-piperidinyl)-1-hydroxy-EDP*[4] | 0.01 |
| N-(2'-(3'-methyl)piperidinylidene)AMDP*[5] | 0.001 |
| N-(2'-(1',3'-diazinylidene))AMDP*[5] | 0.001 |

\* = Compound of the present invention.
[1] ethane-1-hydroxy-1,1-DP
[2] 3-amino propane-1-hydroxy-1,1-DP
[3] dichloromethane DP
[4] EDP = ethane-1,1-diphosphonic acid
[5] AMDP = aminomethane-diphosphonic acid

EXAMPLE 5

Schenk Model

The compounds are evaluated for in vivo bone resorption inhibition and mineralization inhibition in an animal model system known in the field of bone metabolism as the Schenk Model. The general principles of this model system are disclosed in Shinoda et al., *Calcif. Tissue Int.*, 35, 87–99 (1983); and in Schenk et al., *Calcif. Tissue Res.* 11, 196–214 (1973), the disclosures of which are incorporated herein by reference.

Materials and Methods

Animals

Preweaning 17-day-old (30 gms) male Sprague Dawley rats (Charles River Breeding Laboratories) are shipped with their mothers and placed in plastic cages with their mothers upon arrival. At 19 days of age, pups receiving Rat Chow and water ad libitum are randomly allocated into treatment or control groups comprising seven animals per group. On day 1 and again on day 7 all animals are given an intraperitoneal ("IP") injection of Calcein (1% solution in 0.9% saline solution; dosed at 0.2 ml/100 g body weight). On day 4 all animals are given an IP injection of tetracycline hydrochloride (1% solution in 0.9% saline solution; dosed at 0.2 ml/100 g body weight). These compounds label actively mineralizing bone and cartilage.

Dose Solutions and Dosing Procedure

All solutions are prepared for subcutaneous injection in 0.9% normal saline and adjusted to pH 7.4 using NaOH and/or HCl. Dose solution calculation is made by considering the mass of powder (based on molecular weight, hydration) of the active material in mg/kg (body weight) that corresponds to mgP/kg. Concentrations are based on dosing 0.2 ml/100 g body weight. Typically, all compounds are administered at 0.01, 0.1, 1.0 and 10.0 mg P/kg/day for 7 days. Compounds showing activity at 0.1 mg P/kg/day are then tested at logarithmic decrements down to 0.001 mg P/kg/day. Adjustments in dosage based on changes in body weight are made on a daily basis.

Necropsy, Tissue Processing and Histomorphometry

On day 8 after the start of dosing, all animals are sacrificed by IP overdose of pentabarbitol. Tibias are dissected free and placed in 70% ethyl alcohol. One tibia is dehydrated in graded ethanol solutions and embedded in methyl methacrylate as described in Schenk, *Methods of Calcified Tissue Preparation* (G. R. Dickson, Editor; Elsevier Science Publ., The Netherlands; 1984), the disclosures of which are incorporated herein by reference in their entirety. The tibia is sectioned longitudinally through the metaphyseal area. Specimens are stained on one surface with silver nitrate and mounted on microscope slides for evaluation with a Quantimet Image Analyzer (Cambridge Instruments, Inc.) using both incandescent and ultraviolet illumination. Metaphyseal trabecular bone content is measured in the region between the fluorescent label and the growth plate: expressed as percent of total area (bone+marrow). Epiphyseal growth plate width is obtained as the mean value of 10 equally-spaced measurements across the section.

Statistical evaluation of data is made using parametric and non-parametric analysis of variance and Wilcoxons rank sum test to determine a statistically significant effect compared to control animals.

The Schenk model provides data for in vivo bone resorption inhibition by the compounds. The lowest effective (antiresorptive) dose ("LED") for representative compounds tested, as determined by the Schenk model, are provided in Table 2.

TABLE 2

Lowest Effective (Antiresorptive) Dose - Schenk

| Diphosphonate Compound | Schenk LED (mg/P/kg) |
|---|---|
| EHDP[1)] | 1.0 |
| APD[2)] | 0.1 |
| $Cl_2MDP$[3)] | 1.0 |
| 2-(2'-piperidinyl)-EDP*[4)] | 0.01 |
| N-(2'-piperidinyl)-1-hydroxy-EDP*[4)] | 0.01 |
| N-(2'-(3'-methyl)piperidinylidene)AMDP*[5)] | 0.001 |

* = Compound of the present invention.
[1)]ethane-1-hydroxy-1,1-DP
[2)]3-amino propane-1-hydroxy-1,1-DP
[3)]dichloromethane DP
[4)]EDP = ethane-1,1-diphosphonic acid
[5)]AMDP = aminomethane-diphosphonic acid

EXAMPLE 6

Capsules are prepared by conventional methods, comprised as follows:

| Ingredient | Mg per Capsule |
|---|---|
| 2-(2'-piperidinyl)-ethane-1,1-diphosphonic acid | 25 (as mgP) |
| Starch | 55.60 |
| Sodium lauryl sulfate | 2.90 |

The above capsules administered orally twice daily for 6 months substantially reduce bone resorption in a patient weighing approximately 70 kilograms afflicted with osteoporosis. Similar results are obtained when 2-(2'-piperidinyl)-ethane-1,1-diphosphonic acid in the above described capsules is replaced with 2-(3'-piperidinyl)-ethane-1,1-diphosphonic acid; 2-(2'-piperidinyl)-1-hydroxy-ethane-1,1-diphosphonic acid; 2-(3'-piperidinyl)-1-hydroxy-ethane-1,1-diphosphonic acid; N-(2'-(3'-methyl)piperidinylidene)-amino-methane diphosphonic acid; O-(3'-piperidinyl)-oxamethane diphosphonic acid; S-(4'-piperidinyl)-thiomethane diphosphonic acid; or a pharmaceutically acceptable salt or ester of these diphosphonate compounds.

EXAMPLE 7

Tablets are prepared by conventional methods, formulated as follows:

| Ingredient | Mg per tablet |
|---|---|
| 2-(2'-piperidinyl)-1-hydroxy-ethane-1,1-diphosphonic acid | 25 (as mg P) |
| Lactose | 40 |
| Starch | 2.5 |
| Magnesium stearate | 1 |

The above tablets administered orally twice daily for 6 months substantially reduce bone resorption in a patient weighing approximately 70 kilograms afflicted with Paget's disease. Similar results are obtained when 2-(2'-piperidinyl)-1-hydroxy-ethane-1,1-diphosphonic acid in the above described tablets is replaced with 2-(2'-piperidinyl)-ethane-1,1-diphosphonic acid; 2-(3'-piperidinyl)-ethane-1,1-diphosphonic acid; 2-(3'-piperidinyl)-1-hydroxy-ethane-1,1-diphosphonic acid; N-(2'-(3'-methyl)-piperidinylidene)-amino-methane diphosphonic acid; O-(4'-piperidinyl)oxamethane diphosphonic acid; S-(3'-piperidinyl)-thiomethane diphosphonic acid; or a pharmaceutically acceptable salt or ester of these diphosphonate compounds.

EXAMPLE 8

Injectable solutions are prepared by conventional methods using 1.0 ml of physiological saline solution and 0.07 mg P of N-(2'-(3'-methyl)-piperidinylidene)-amino-methane diphosphonic acid, adjusted to pH=7.4.

One injection, one time daily for 4 days, results in appreciable alleviation of hypercalcemia of malignancy in patients weighing approximately 70 kilograms.

EXAMPLE 9

Patients weighing approximately 70 kilograms who are clinically diagnosed as suffering from hypercalcemia of malignancy are administered 0.07 mg P of 2-(2'-piperidinyl)-1-hydroxy-ethane-1,1-diphosphonic acid, or its pharmaceutically acceptable salt or ester, by a 2½ hour intravenous infusion one time daily for 4 days. This treatment results in an appreciable alleviation of the hypercalcemia of malignancy.

What is claimed is:

1. A heterocycle-substituted diphosphonic acid, or a pharmaceutically-acceptable phosphonic acid salt or ester thereof, substituted with a nitrogen-containing six membered ring heterocycle, having the general structure:

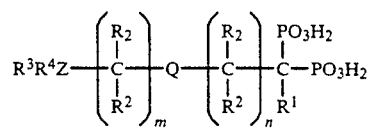

wherein:
(a) Z is a nitrogen-containing six membered ring heterocycle moiety selected from piperidinyl, diazinyl, and triazinyl;
(b) Q is a covalent bond or a moiety selected from the group consisting of oxygen, sulfur, or —$NR^2$—;
(c) m is the integer 0 and n is an integer from 0 to 10;
(d) $R^1$ is selected from the group consisting of hydrogen; halogen; alkyl having from 1 to 6 carbon atoms; phenyl; benzyl; hydroxy, and the $C_1$–$C_6$ esters thereof; unsubstituted amino, and $C_1$–$C_6$ acylamino; amino and $C_1$–$C_6$ acylamino substituted with one alkyl group having from 1 to 6 carbon atoms; amino substituted independently with two alkyl groups having from 1 to 6 carbon atoms; ammonium substituted independently with three alkyl groups having from 1 to 6 carbon atoms, having a pharmaceutically-acceptable counter-ion; and $-CO_2H$, the pharmaceutically-acceptable salts thereof, the $C_1-C_6$ esters thereof, the unsubstituted amide thereof, and the amide thereof substituted with one or two alkyl groups having from 1 to 6 carbon atoms; except that when n=0 and Q is oxygen, sulfur or nitrogen then $R^1$ is selected from the group consisting of hydrogen; alkyl having from 1 to 6 carbon atoms; phenyl; benzyl; $-CO_2H$, the pharmaceutically-acceptable salts thereof, the $C_1-C_6$ esters thereof, the unsubstituted amide thereof, and the amide thereof substituted with one or two alkyl groups having from 1 to 6 carbon atoms;

(e) $R^2$ is selected from the group consisting of hydrogen, methyl, ethyl, and propyl; and (f) $R^3$ and $R^4$ are substituents on one or more carbon atoms of said heterocycle, independently selected from the group consisting of hydrogen; halogen; alkyl having from 1 to 3 carbon atoms; unsubstituted amino, and $C_1-C_3$ acylamino; amino and $C_1-C_3$ acylamino, substituted with one alkyl group having from 1 to 3 carbon atoms; amino substituted independently with two alkyl groups having from 1 to 3 carbon atoms; ammonium substituted independently with three alkyl groups having from 1 to 3 carbon atoms; hydroxy, or the $C_1-C_3$ esters thereof; ether having from 1 to 3 carbon atoms, having a pharmaceutically-acceptable counter-ion; $-CO_2H$, the pharmaceutically-acceptable salts thereof, the $C_1-C_3$ esters thereof, the unsubstituted amide thereof, and the amide thereof substituted with one or two alkyl groups having from 1 to 3 carbon atoms; and nitro.

2. A diphosphonic, acid or a pharmaceutically-acceptable phosphonic acid salt or phosphonic acid ester thereof, according to claim 1 wherein the Z moiety is selected from piperidinyl; 1,3-diazinyl; and 1,4-diazinyl.

3. A piperidine-substituted diphosphonic acid, or a pharmaceutically-acceptable phosphonic acid salt or phosphonic acid ester thereof, having the general structure:

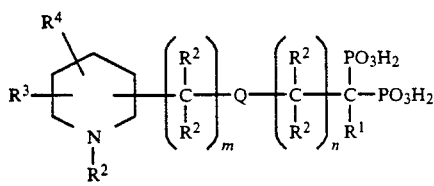

wherein:
(a) Q is a covalent bond or a moiety selected from the group consisting of oxygen, sulfur, or $-NR^2-$;
(b) m is the integer 0 and n is an integer from 0 to 10;
(c) $R^1$ is selected from the group consisting of hydrogen; halogen; alkyl having from 1 to 6 carbon atoms; phenyl; benzyl; hydroxy, and the $C_1-C_6$ esters thereof; unsubstituted amino, and $C_1-C_6$ acylamino; amino and $C_1-C_6$ acylamino substituted with one alkyl group having from 1 to 6 carbon atoms; amino substituted independently with two alkyl groups having from 1 to 6 carbon atoms; ammonium substituted independently with three alkyl groups having from 1 to 6 carbon atoms, having a pharmaceutically-acceptable counter-ion; and $-CO_2H$, the pharmaceutically-acceptable salts thereof, the $C_1-C_6$ esters thereof, the unsubstituted amide thereof, and the amide thereof substituted with one or two alkyl groups having from 1 to 6 carbon atoms; except that when n=0 and Q is oxygen, sulfur or nitrogen, then $R^1$ is selected from the group consisting of hydrogen; alkyl having from 1 to 6 carbon atoms; phenyl; benzyl; and $-CO_2H$, the pharmaceutically-acceptable salts thereof, the $C_1-C_6$ esters thereof, the unsubstituted amide thereof, and the amide thereof substituted with one or two alkyl groups having from 1 to 6 carbon atoms;

(d) $R^2$ is selected from the group consisting of hydrogen, methyl, ethyl, and propyl;

(e) $R^3$ and $R^4$ are substituents on one or more carbon atoms of said heterocycle, independently selected from the group consisting of hydrogen; halogen; alkyl having from 1 to 3 carbon atoms; unsubstituted amino, $C_1-C_3$ acylamino; amino and $C_1-C_6$ acylamino substituted with one alkyl group having from 1 to 3 carbon atoms; amino substituted independently with two alkyl groups having from 1 to 3 carbon atoms; ammonium substituted independently with three alkyl groups having from 1 to 3 carbon atoms, having a pharmaceutically-acceptable counter-ion; hydroxy, or the $C_1-C_6$ esters thereof; ether having from 1 to 3 carbon atoms; and $-CO_2H$, the pharmaceutically-acceptable salts thereof, the $C_1-C_3$ esters thereof, the unsubstituted amide thereof, and the amide thereof substituted with one or two alkyl groups having from 1 to 3 carbon atoms; and nitro;

and wherein further when m=0 and Q is oxygen, nitrogen or sulfur, then Q is bonded to the piperidine ring at a carbon atom not bonded directly to the nitrogen atom in the piperidine ring except that when Q is nitrogen then Q may also be bonded to the piperidine ring by a piperidinylidene structure.

4. A piperidine-substituted diphosphonic acid, or a pharmaceutically-acceptable phosphonic acid salt or phosphonic acid ester thereof, according to claim 3 having the general structure:

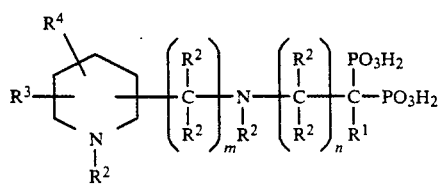

wherein m is 0 and n is 0 or 1.

5. A piperidine-substituted diphosphonic acid, or a pharmaceutically-acceptable phosphonic acid salt or phosphonic acid ester thereof, according to claim 5 having the general structure:

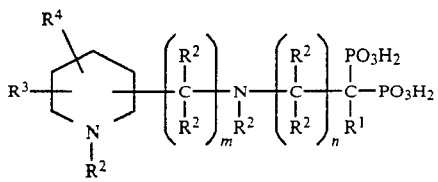

wherein m+n=0 or 1; $R^1$ is selected from the group consisting of hydrogen, chloro, methyl, ethyl, hydroxy, unsubstituted amino, (N-methyl)amino, (N,N-dimethyl)amino, —$CO_2H$ and the pharmaceutically-acceptable salts thereof, —$CO_2CH_3$, and —$CONH_2$, except that when n=0 then $R^1$ is selected from the group consisting of hydrogen, methyl, ethyl, —$CO_2H$ and the pharmaceutically-acceptable salts thereof, —$CO_2CH_3$ and —$CONH_2$; each $R^2$ is independently selected from hydrogen or methyl; and $R^3$ and $R^4$ are substituents independently selected from the group consisting of hydrogen, methyl, ethyl, hydroxy, unsubstituted amino, (N-methyl)amino, (N,N-dimethyl)amino, chloro, methoxy, ethoxy, nitro, —$CO_2H$ and the pharmaceutically-acceptable salts thereof, —$CO_2CH_3$, —$CONH_2$, and combinations thereof.

6. A piperidine-substituted diphosphonic acid, or a pharmaceutically-acceptable phosphonic acid salt or phosphonic acid ester thereof, having the general structure:

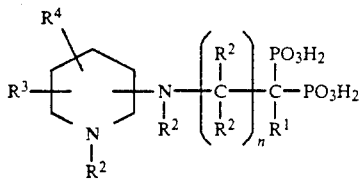

wherein n=0 or 1; $R^1$ is selected from the group consisting of hydrogen, methyl, chloro, amino and hydroxy, except that $R^1$ is selected from hydrogen or methyl when n=0; each $R^2$ is independently selected from the group consisting of hydrogen and methyl; and $R^3$ and $R^4$ are substituents independently selected from the group consisting of hydrogen, methyl, amino, chloro, methoxy, hydroxy and combinations thereof.

7. A piperidine-substituted diphosphonic acid, or a pharmaceutically acceptable phosphonic acid salt or phosphonic acid ester thereof, according to claim 6 having the general structure:

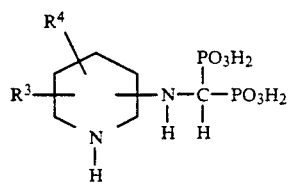

wherein $R^3$ and $R^4$ are substituents independently selected from the group consisting of hydrogen and methyl.

8. A piperidine-substituted diphosphonic acid, or a pharmaceutically-acceptable phosphonic acid salt or phosphonic acid ester thereof, according to claim 6 having the piperidinylidene structure:

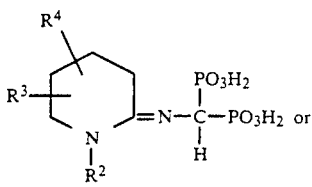

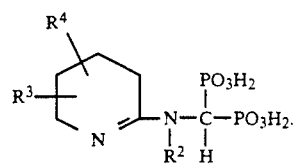

9. A pharmaceutical composition comprising:
(a) a safe and effective amount of a heterocycle-substituted diphosphonic acid, salt or ester according to claim 1; and
(b) a pharmaceutically-acceptable carrier.

10. A pharmaceutical composition comprising:
(a) a safe and effective amount of a piperidine-substituted diphosphonic acid, salt or ester according to claim 3; and
(b) a pharmaceutically-acceptable carrier.

11. A pharmaceutical composition comprising:
(a) a safe and effective amount of a piperidine-substituted diphosphonic acid, salt or ester according to claim 7; and
(b) a pharmaceutically-acceptable carrier.

12. A pharmaceutical composition comprising:
(a) a safe and effective amount of a piperidine-substituted diphosphonic acid, salt or ester according to claim 8; and
(b) a pharmaceutically-acceptable carrier.

13. A pharmaceutical composition comprising:
(a) a safe and effective amount of a piperidine-substituted diphosphonic acid, salt or ester according to claim 2, and
(b) a pharmaceutically-acceptable carrier.

14. A method for treating phathological conditions associated with abnormal calcium and phosphate metabolism in humans or lower animals, said method comprising administering to a human or lower animal in need of such treatment a safe and effective amount of a piperidine-substituted diphosphonic acid, salt or ester compound of claim 7.

15. A method for treating pathological conditions associated with abnormal calcium and phosphate metabolism in humans or lower animals, said method comprising administering to a human or lower animal in need of such treatment a safe and effective amount of a heterocycle-substituted diphosphonic acid, salt or ester compound of claim 8.

16. The compound N-(2'-(3'-methyl)-piperidinylidene)-aminomethane diphosphonic acid, or a pharmaceutically-acceptable phosphonic acid salt or phosphonic acid ester thereof.

* * * * *

UNITED STATES PATENT AND TRADEMARK OFFICE
CERTIFICATE OF CORRECTION

PATENT NO. : 5,071,840
DATED : December 10, 1991
INVENTOR(S) : Frank H. Ebetino & James J. Benedict It is certified that error appears in the above-indentified patent and that said Letters Patent is hereby corrected as shown below:

In Claim 1, Column 20, lines 59 & 60, the terms ", diazinyl, and triazinyl," should be deleted and the term -- and piperidinylidene; -- should be inserted therefor.

In Claim 2, Column 21, lines 43 & 44, the terms "; 1,3-diazinyl; and 1,4-diazinyl." should be deleted and the term -- and piperidinylidene. -- should be inserted therefor.

In Claim 3, Column 22, line 24, the term "heterocycle," should be deleted and the term -- piperidinyl ring, -- should be inserted therefor.

Signed and Sealed this

Sixteenth Day of August, 1994

Attest:

BRUCE LEHMAN

*Attesting Officer*  *Commissioner of Patents and Trademarks*